United States Patent
Claude et al.

(10) Patent No.: US 8,426,808 B2
(45) Date of Patent: Apr. 23, 2013

(54) METHOD OF MASS SPECTROMETRY

(75) Inventors: Emmanuelle Claude, Cheshire (GB); Marten F. Snel, Cheshire (GB); Johannes Petrus Cornelis Vissers, Huizen (NL); Keith Richardson, Derbyshire (GB)

(73) Assignee: Waters Technologies Corporation, Milford, MA (US)

( * ) Notice: Subject to any disclaimer, the term of this patent is extended or adjusted under 35 U.S.C. 154(b) by 54 days.

(21) Appl. No.: 13/146,681

(22) PCT Filed: Feb. 8, 2010

(86) PCT No.: PCT/GB2010/050194
§ 371 (c)(1),
(2), (4) Date: Sep. 15, 2011

(87) PCT Pub. No.: WO2010/089611
PCT Pub. Date: Aug. 12, 2010

(65) Prior Publication Data
US 2012/0326019 A1    Dec. 27, 2012

Related U.S. Application Data

(60) Provisional application No. 61/181,708, filed on May 28, 2009.

(30) Foreign Application Priority Data

Feb. 6, 2009  (GB) .................................... 0901933.2
Apr. 15, 2009 (GB) .................................... 0906465.0

(51) Int. Cl.
*H01J 49/00* (2006.01)
*H01J 37/256* (2006.01)

(52) U.S. Cl.
USPC ........ 250/282; 250/281; 250/286; 250/492.1; 250/492.2

(58) Field of Classification Search .................. 250/282, 250/281, 286, 492.1, 492.2
See application file for complete search history.

(56) References Cited

U.S. PATENT DOCUMENTS

| | | | |
|---|---|---|---|
| 7,057,168 B2 * | 6/2006 | Miller et al. ................... | 250/287 |
| 2005/0230611 A1 * | 10/2005 | Denny et al. ................... | 250/282 |
| 2006/0063145 A1 | 3/2006 | Suckau et al. | |
| 2007/0069122 A1 | 3/2007 | Augustin et al. | |

OTHER PUBLICATIONS

Hanselmann et al; "Concise Representation of Mass Spectrometry Images by Probabilistic Latent Semantic Analysis" Anal. Chem. 2008, 80, 9649-9658.

Deininger et al; MALDI Imaging Combined with Hierarchial Clustering as a New Tool for the Interpretation of Complex Human Cancers; Journal of Proteome Research 2008, 7, 5230-5236.

(Continued)

*Primary Examiner* — Nikita Wells
(74) *Attorney, Agent, or Firm* — Waters Technologies Corp

(57) ABSTRACT

This invention comprises a method of imaging of a substrate in which a sample of interest is first ionized at multiple known positions whereafter a mass spectrum of the ionized sample at each of the multiple known positions is produced using a Mass Spectrometer. An overall spectrum for the whole sample is then created, and a number of peaks within the overall spectrum is selected. A scan distribution for at least some of the selected peaks is created, and the scan distributions are compared to identify correlations between different analytes within the sample.

16 Claims, 1 Drawing Sheet

OTHER PUBLICATIONS

Trim, et al; "Matrix-assisted laster desorption/ionisaiton mass spectrometry imaging of lipids in rat brain tissue with integrated unsupervised and supervised multivariant statistical analysis"; Rapid Commun. Mass Spectrom, 2008, 1503-1509.

Stoeckli, et al; "Molecular imaging of amyloid B peptides in mouse brian sections using mass spectrometry"; Analytical Biochemistry 311 (2002) 33-39.

PCT International Search Report, Form ISA/210 for PCT/GB2010/0050194, dated Jun. 16, 2010.

* cited by examiner

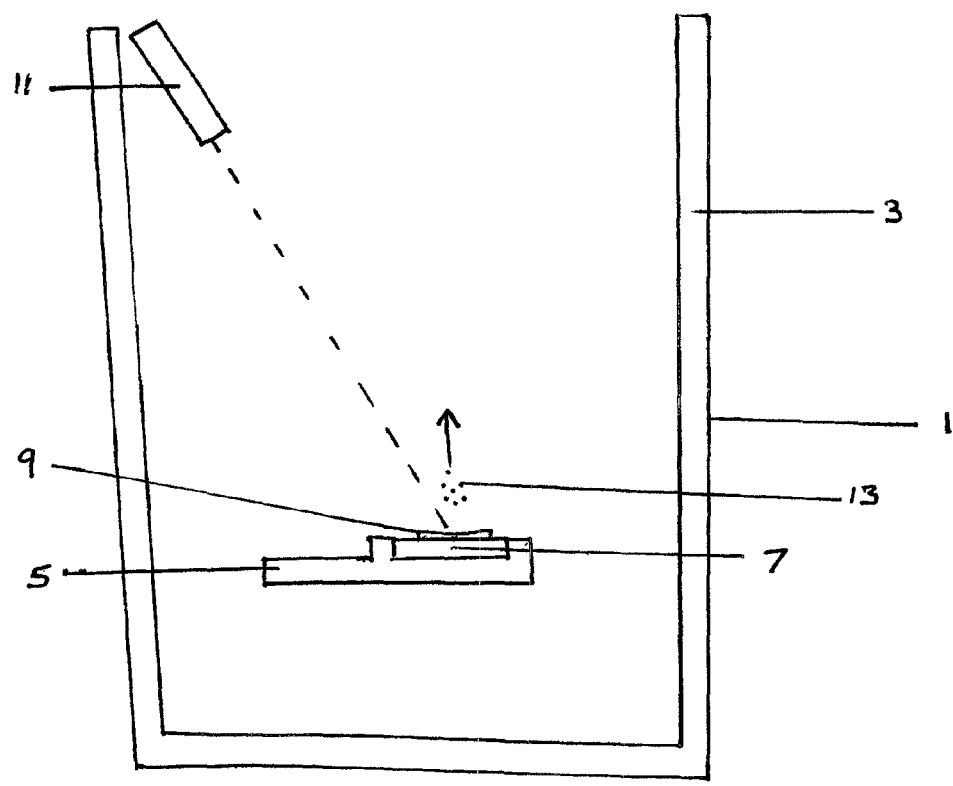

METHOD OF MASS SPECTROMETRY

BACKGROUND ART

Mass spectrometric imaging is an emerging tool in post genomic sciences such as proteomics, lipidomics and metabolomics.

Lipidomics, after genomics and proteomics, is a rapidly expanding research field that studies cellular lipidomes and the organisational hierarchy of lipid and protein constituents mediating life processes. Lipidomics is greatly facilitated by recent advances in, and novel applications of, electrospray ionization mass spectrometry (ESI/MS).

Moreover, Matrix Assisted Laser Desorption Ionization (MALDI) imaging mass spectrometry enables biomolecules to be analyzed directly from tissue sections, providing information on spatial distribution of analytes within the tissue sample. This involves the analysis of the differences in the chemical makeup of different areas of the substrate. Irradiation of areas of the substrate of interest by laser light in the presence of a matrix material produces ions that can be analysed by mass spectrometry, typically Time of Flight mass spectrometry (ToF).

Limitation of MALDI imaging is the complexity of the data collected, especially in the case of a non-targeted, open platform experiment.

To overcome this limitation, MALDI imaging data is typically arranged into different sections, a way of reducing the data complexity. In this case the ions from areas of the substrate that are in close relationship are added together to produce overall spectra for these sections within the substrate. However, using this procedure means that data can be lost and that differences between the chemical make up of areas within each section of the substrate may not be identified.

It is therefore desirable to find a method of analysis which will use all the data and differentiate between all the different areas of the substrate in an efficient way to identify information of interest relating to the sample.

SUMMARY OF THE INVENTION

A preferred embodiment of the current invention consists of a method of imaging of a substrate comprising the steps of:
Ionizing a sample of interest at multiple known positions upon the sample,
producing a mass spectrum of the ionized sample at each of said multiple known positions using a Mass Spectrometer,
creating an overall spectrum for the whole sample, selecting a number of peaks within the overall spectrum,
creating a scan distribution for at least some of said selected peaks, and
comparing the scan distributions to identify correlations between different analytes within the sample.

Preferably, each predetermined position is identifiable by a set of coordinates such that the ionized sample is produced from said predetermined position.

Preferably, the Mass Analyser is a Time of Flight Mass Analyser.

Preferably the ionisation of the sample is performed using MALDI.

Preferably, the method further comprising the step of generating IMS data for the ions produced at each predetermined position.

Preferably, the method further comprises the step of generating MS and MS/MS data for the ions produced at each predetermined position.

Preferably, the method further comprising the step of removing minor variations in spectral noise by subtraction of X% of the intensity of the peaks.

Preferably, X is up to 15%, More Preferably X is in the range 1-10%. Most preferably X is in the range 3-7%.

Preferably, the scan distributions are normalised to scale peaks relative to each other.

Preferably, the method further comprises filtering said overall mass spectral data to perform background subtraction.

Preferably, the substrate is a tissue sample.

Preferably, the method is used for the analysis of information or products relating to drugs and drug metabolites within said tissue information.

Preferably, the comparison of scan distributions comprises performing Principal Component Analysis.

Taking a "holistic" approach, numerous molecules including, endogenous (i.e. peptides, lipids) or exogenous (i.e. drug and its metabolites, matrix), can be detected within the tissue. When the data is presented as a series of images, one has to scan all masses to observe the differences, and similarities, between molecule localizations An embodiment of the invention will now be described, by way of example, with reference to the accompanying drawings, in which:

FIG. 1 is a schematic view of a MALDI ion source

DETAILED DESCRIPTION OF THE PREFERRED EMBODIMENT

The preferred embodiment of the current invention comprises the steps of:
Ionizing a sample of interest at multiple known positions upon the sample,
producing a mass spectrum of the ionized sample at each of said multiple known positions using a Mass Spectrometer,
creating an overall spectrum for the whole sample Select a number of peaks within the overall spectrum,
creating a scan distribution for at least some of said selected peaks, and
comparing the scan distributions to identify correlations between different analytes within the sample.

Turning to FIG. 1, this shows mass spectrometric apparatus (1). The apparatus comprises a housing (3) having a sample holder (5) for holding a sample plate (7). The sample plate (7) has been loaded with a sample (9). A laser (11) is disposed within the housing such that, when in use, the laser is orientated to irradiate the sample (9) at predetermined points upon the sample holder (5) with laser light. Upon the radiation of the sample with laser light, ions (13) are formed from the predetermined points upon the sample. These ions are then transported into an analysis section of a mass spectrometer.

In the preferred embodiment ions can be directed into an ion guide or ion tunnel for transporting into a mass analysis system. Examples of suitable systems included a QToF type mass spectrometer or a Waters Synapt HDMS mass spectrometer. In one embodiment of the invention, the time of flight of the ions can be determined using a ToF mass analyser. In another embodiment of the invention the ion mobility of the ions is measured in addition to their Time Of Flight. This may allow differentiation of ions of different species that may have the same mass.

In a less preferred embodiment, ions produced can be transported directly into an axial time of flight drift tube using a pusher device within the ion source in a way similar to that in the Micromass MALDI Micro mass spectrometer, In one embodiment of the invention the ions may be passed through a collision cell, and fragment ions produced within the collision cell may be analysed by the disclosed methods.

In a further embodiment of the invention the ions may be passed through a drift cell, and the ion mobility of ions may be measured before analysis by the time of flight analyser. The use of ion mobility data may be useful to distinguish between different ions of the same mass within the tissue sample under analysis by the disclosed methods.

In one embodiment of the invention, the sample holder may be movable such that when using a stationary laser, the laser can irradiate different areas of the sample upon the sample holder. In an alternative embodiment of the invention the laser may be movable but the sample holder may be stationary so the laser can irradiate different areas of the sample upon the sample holder.

A location indicator should be assigned for each predetermined position within the sample. This may be a coordinate, scan number or any other form of location indicator.

In the preferred embodiment of the invention the sample is a biological sample.

In another embodiment of the invention the sample may be adapted and designed for MALDI mass spectrometric analysis.

In less preferred embodiments of the invention the sample may be adapted and designed for secondary ion mass spectrometry. In further embodiments of the invention the sample may be designed for any other method of imaging of a sample.

In one embodiment of the invention the laser may be pulsed so that individual spots upon the sample may be irradiated consecutively and the spectra at each predetermined point may be produced from ions produced by either one, or multiple pulses of the laser.

In an alternative embodiment of the invention the laser may continuously irradiate the sample whilst the sample and/or laser are moving with respect to each other.

In a further embodiment of the invention, the laser may irradiate ions for a substantial, though not continuous, proportion of the time whilst the sample and laser are moving with respect to each other.

The laser may be any type of suitable laser. An example of a suitable laser is a solid state YaG laser.

An overall spectrum may be generated by the addition of the spectra for each predetermined position that has been acquired across the whole of the sample.

Once the overall spectrum has been generated, all peaks or a number of the peaks can be selected for further analysis. Each peak represents a particular analyte.

In the most preferred embodiment, the peaks selected are the 'n' most intense peaks in the overall spectrum.

In less preferred embodiments the peaks selected may be any peaks across the overall spectrum.

A 'scan distribution' is created for each selected analyte across the sample. This is created by plotting the intensity of each peak on the Y axis against a location indicator on the X axis for each point on the surface.

In a preferred embodiment, ion mobility dimension will be taken into account and a selected drift time range can be selected for each m/z peak. This can be done after an algorithm Apex 3D for example is applied to the data set.

In the preferred embodiment the scan distributions can be smoothed and background 'noise' may be subtracted using mass spectral deconvolution programs.

In the preferred embodiment, spectral noise can be removed by the subtraction of a small percentage X of the intensity of the scan distribution can be produced. Preferably X is less than 15%. More preferably X is in the range 1-10%. Most preferably X is in the range 3-7%.

In the preferred embodiment the scan distribution can be normalised.

The scan distributions of the 'n' selected peaks are then compared to identify correlations between the different analytes within the sample. Preferably, n is in the range 10-100000.

In one embodiment data relating to scan distributions that can be identified as correlating with other scan distributions s may be kept and data relating to scan distributions that can't be identified as correlating with other scan distributions may be excluded as desired.

In one embodiment the data produced by the disclosed methods may be imput into statistical software packages using multivariate statistics to identify relationships between different analytes across the substrate. Examples of software packages suitable for this include Spotfire and Ez info.

The present invention utilises an unsupervised statistical approach to examine the entire dataset, rather than a more traditional approach where the dataset has been sectioned into different regions of interest. This does not involve the normal approach of obtaining "n" spectra from "n" regions and comparing those to highlight molecules more abundant in one region compared to another. In the present method, the distributions of molecules throughout the entire tissue section are compared to enable a statistical algorithm to group molecules which have similar scan distributions which represent similar localization. Rather than comparing MS spectra the method compares scan distributions for each of the molecules that is extracted where each scan represents a particular predetermined location.

Preliminary Data

MALDI imaging data obtained from the analyses of frozen mouse uterus tissue sections have been used to demonstrate the statistical approach. Data from both MALDI MS imaging as well as MALDI IMS-MS imaging has been used to test the strategy. The use of ion-mobility provides an extra dimension of separation for very complex sample datasets. The data interpretation workflow starts with the extraction of the scan distribution for each m/z value. For each m/z value, the scan distribution represents its pixilated image without taking into account their spatial coordinate. After processing which may include; smoothing, background subtraction, removal of noise and/or normalization, the dataset can be interrogated using different multivariate statistical algorithms, such as clustering or Principal Component Analysis (PCA). PCA can rapidly group m/z values which exhibit similar distributions throughout the tissue, without prior knowledge. This approach easily facilitates, for example, the differentiation of exogenous molecules from endogenous molecules, as well as the identification of structural features within the image.

Other Embodiments

It will be apparent that various modifications may be made to the particular embodiments discussed above without departing from the scope of the invention.

The invention claimed is:

1. A method of analysis of data produced from the imaging of a substrate comprising the steps of:
ionizing a sample of interest with laser light at multiple predetermined positions upon the sample,
producing a mass spectrum of the ionized sample at each of said multiple predetermined positions using a Mass Analyser,
creating an overall spectrum for the whole sample,
selecting a number of peaks within the overall spectrum, creating a scan distribution for at least some of said selected peaks, and comparing the scan distributions to identify correlations between different analytes within the sample.

2. A method as claimed in claim 1 wherein each predetermined position is identifiable by a set of coordinates such that the ionized sample is produced from said predetermined position.

3. A method as claimed in claim 1 or 2 wherein said Mass Analyser is a Time of Flight Mass Analyser.

4. A method as claimed in claims 1-3 wherein said ionisation of sample is performed using MALDI.

5. A method as claimed in, claim 1, further comprising the step of generating IMS data for the ions produced at each predetermined position.

6. A method as claimed in claim 1, further comprising the step of generating MSMS data for the ions produced at each predetermined position.

7. A method as claimed in claim 1, further comprising the step of removing minor variations in spectral noise by subtraction of X% of the intensity of the peaks.

8. A method as claimed in claim 7, wherein X is a value up to 15%.

9. A method as claimed in claim 8, wherein X is in the range 1-10%.

10. A method as claimed in claim 9, wherein X is in the range 3-7%.

11. A method as claimed in claim 1, wherein said scan distributions are normalised to scale peaks relative to each other.

12. A method as claimed in claim 1, further comprising filtering said overall mass spectral data to perform background subtraction.

13. A method as claimed in claim 1, wherein the substrate is a tissue sample.

14. A method as claimed in claim 13 for the analysis of information or products relating to drugs and drug metabolites within said tissue information.

15. A method as claimed in claim 1 wherein said comparison of scan distributions comprises performing Principal Component Analysis.

16. A method of analysis of data produced from the imaging of a substrate substantially as claimed in claim 1.

* * * * *